United States Patent [19]

Showalter

[11] Patent Number: 5,391,554
[45] Date of Patent: Feb. 21, 1995

[54] DIHYDRO- AND TETRAHYDRONAPHTHYRIDINES

[75] Inventor: Howard D. H. Showalter, Ann Arbor, Mich.

[73] Assignee: Warner-Lambert Company, Morris Plains, N.J.

[21] Appl. No.: 942,244

[22] Filed: Sep. 9, 1992

[51] Int. Cl.$^6$ ..................... A61K 31/44; C07D 471/04
[52] U.S. Cl. ..................................... 514/300; 546/122
[58] Field of Search .......................... 546/122; 514/300

[56] References Cited

U.S. PATENT DOCUMENTS 4,329,349 5/1982 Damon et al. ...................... 924/256

FOREIGN PATENT DOCUMENTS 0355750 2/1990 European Pat. Off. .

OTHER PUBLICATIONS

Adams, G. E., et al., Chemotherapy (1975); 7:187–206.
Adams, et al., Biochemical and Biophysical Research Communications (1963); 12(6):473–477.
Foster, et al., British Journal of Radiology (1973); 46:234–235.
Asquith, et al., Radiation Research (1974); 60:108–118.
Hur, et al., Radiation Research (1984); 97:546–555.
Kato, et al., Anticancer Research (1988); 8:239–244.
Sakamoto, et al., Chem. Pharm. Bulletin (1986); 34(5) pp. 2018–2023.
Otiai, et al., J. Pharm. Soc. Japan (1938); 58:764–770.
Ikekawa, N. et al., Chem. Pharm. Bulletin (1958) 6(3) pp. 263–269.
Combret, et al., Tetrahedron (1991); 47(45) pp. 9369–9382.
Combret, et al., Chemistry Letters (1991); pp. 125–128.
Sigova, et al., Khimiya Geterotsiklicheskikh Soedinenii (1984); 6:783–785.
Nietsch, et al., Arch. Pharm. (Weinheim) (1985); 318:175–177.
Tada, et al., J. Heterocyclic Chemistry (1989); 26:45–48.
Baldwin, et al., Journal of Organic Chemistry (1978); 43(25):4878–4880.
Berge, et al., Journal of Pharmaceutical Sciences, "Pharmaceutical Salts", (1977); 66(1):1–19.
Abdulla, et al., Tetrahedron (1979); 35:1675–1735.
Rylander, P. N., Aldrichimica Acta (1979); 12(3):53–58.
Shizuta, et al., Methods in Enzymology (1980); 66:159–165.
Chou, et al., Adv. Enzyme Regul. (1984); 22:27–55.

Primary Examiner—Raymond J. Henley, III
Assistant Examiner—Phyllis G. Spivack
Attorney, Agent, or Firm—Elizabeth M. Anderson

[57] ABSTRACT

This invention concerns novel dihydro- and tetrahydronaphthyridines useful for enhancing the lethal effects on tumor cells to treatment causing DNA-damaging activity as with ionizing radiation or with a chemotherapeutic agent.

9 Claims, No Drawings

DIHYDRO- AND TETRAHYDRONAPHTHYRIDINES

BACKGROUND OF THE INVENTION

The present invention relates to certain novel dihydro- and tetrahydronaphthyridines useful for sensitizing tumor cells to the lethal effects of DNA-damaging agents such as ionizing radiation and chemotherapeutic agents.

Extensive evidence indicates that the radioresistance of many solid tumors is directly proportional to their hypoxic fractions. In the presence of oxygen the amount of cell kill achievable by ionizing radiation is increased.. When well oxygenated cells are irradiated, irreparable lesions occur resulting from the reaction between radiation-damaged DNA and oxygen. Under hypoxic conditions such as those found in solid tumors, the initial damage that occurs from ionizing radiation is more readily repaired than that which occurs in oxic cells and ultimately leads to tumor regrowth.

The presence of hypoxic cells in tumor tissue has been demonstrated repeatedly in animal tumors, and their presence results in resistance to radiation, which makes cures with a single dose of x-rays difficult or impossible. (See Adams GE, et al, *Chemotherapy* 1975;7:187-206, Plenum Press, New York.) This problem is compounded by the fact that radiotherapy continues to be a major method for treating cancer patients. Approximately 50% to 60% of all cancer patients undergo some type of radiotherapy. However, the presence of these radio-resistant cells results in about 30% of these patients succumbing to a lack of control of the primary disease. Therefore, a need exists for a compound which renders solid tumors more susceptible to the lethal effects of radiation.

To overcome the problem of the resistance of hypoxic tumor cells to radiation therapy, patients have been irradiated in hyperbaric oxygen chambers. Although much experience has been gathered with this method, it is cumbersome and slow to use. Moreover, the shutdown of blood vessels is also a serious problem associated with this method.

Another solution which has been tried is the use of chemical agents which simulate the action of oxygen in their ability to sensitize hypoxic tumor cells to radiation. In 1963, Adams, et al (*Biochem Biophy Res Comm* 1963;12:473), proposed that the ability of compounds to sensitize hypoxic bacterial cells is directly related to their electron affinity. This idea has been generally verified and has aided the search for more active compounds.

In 1973, J. L. Foster and R. L. Wilson (*Brit J Radiol* 1973; 46: 234) discovered the radiosensitizing action of the antiprotozoal drug metronidarole (2-methyl-5-nitro-1H-imidazole-1-ethanol). Metronidazole is active both in vitro and in vivo as a radiosensitizer.

Another antiprotozoal drug, misonidazole (α-(methoxymethyl)-2-nitro-1H-imidazole-1-ethanol) has also recently proven to be of value as a radiosensitizer for hypoxic tumor cells (Asquith J, et al, *Rad Res* 1974;60:108).

Both metronidazole and misonidazole are effective as radiosensitizers for hypoxic cells in vivo. However, both compounds exhibit serious adverse central nervous system (CNS) side effects when administered to mice. They exhibit peripheral neuropathy effects and convulsions in mice and their CNS toxicity is thus a limiting factor for their use in humans. Nevertheless, the activity of these compounds as radiosensitizers has led to further interest and has spurred the search for additional compounds with similar activity but with diminished side effects.

Radiotherapy is now routinely given as a series of small doses of radiation (fractionated treatment) in an effort to minimize normal tissue damage and allow for tumor reoxygenation. This regimen renders the tumor more sensitive to successive radiation doses. However, substantial repair of radiation-induced damage can also occur between these small doses of radiation. This is illustrated by cell survival plots of nonexponential cell kill, which is sometimes referred to as the shoulder region of an x-ray dose-response curve (i.e., cells surviving the first dose of radiation respond as unirradiated cells to the second fraction, etc). The use of a fractionated regimen provides a small therapeutic gain with each fraction resulting in an improved gain over the course of the treatment. Inhibitors of this repair process, i.e., shoulder-modifying agents such as N-methylformamide, have been shown to sensitize tumors to the lethal effects of radiation.

Some cells when exposed to radiation do not immediately succumb to the lethal effects of radiation. This delay in toxicity, usually referred to as potentially lethal damage (PLD), accounts for some of the postirradiation toxicity that is seen when cells are treated with x-rays. PLD is DNA damage, which may be lethal if the cell attempts to replicate, but which is repaired if the cells are prevented from replicating. Compounds such as 3-aminobenzamide (PLDR inhibitors) have been shown to inhibit this postirradiation repair process, thereby sensitizing cells to the lethal effects of radiation.

Ben Hur, et al (*Rad Res* 1984; 97: 546), demonstrated that in certain cell lines the repair of damage caused by exposure to DNA-damaging agents such as ionizing radiation, was inhibited by 3-aminobenzamide. This inhibition of repair led to an enhanced killing of these cells by the damaging agents. The compounds examined are also inhibitors of poly (ADP-ribose) synthetase or adenosine diphosphate ribosyl polymerase (ADPRP), an enzyme that is elevated when cells are exposed to alkylating agents and to ionizing radiation, and is thought to play a role in the repair of DNA damage. Therefore, inhibitors of poly (ADP-ribose) synthetase can potentiate the lethal effects of DNA-damaging agents such as ionizing radiation and also potentiate for use in the methods of the present invention certain chemotherapeutic agents such as bleomycin (Kato T, Suzumura Y, Fukushima M, *Anticancer Research* 1988;8:239) and the like.

The present invention provides compounds which enhance the lethal effects of ionizing radiation thereby making tumors more sensitive to radiation therapy. These compounds work by affecting the processes involved in the repair of radiation-induced DNA damage. Since the compounds of the invention also inhibit poly-(ADP-ribose)synthetase they have utility as potentiators of certain chemotherapeutic agents as described above by T. Kato, et al.

U.S. Pat. No. 07/758,180 (EPA 355750) discloses substituted dihydroisoquinolinones and related compounds as potentiators of the lethal effects of radiation and certain chemotherapeutic agents.

T. Sakamoto, et al. (*Chem Pharm Bull* 1986;34:2018-23) covers the iodination and subsequent dehydroxychlorination of 1, 6-naphthyridin-5 (6H) -one producing 5-chloro-8-iodo-1,6-naphthyridine which was converted to the 5-methoxy derivative.

E. Otiai and K. Miyaji (*J Pharm Soc Japan* 1938;58:764-70) and N. Ikekawa (*Chem Pharm Bull* 6:263-269) cover the synthesis of 1,6-naphthyridines.

Y. Combret, et al. (*Tetrahedron* 1991;47:9369) discuss a 1,6-naphthyridinone structure (see also Y. Combret, et al. (*Chemistry Letters* 1991;125-8)).

U.S. Pat. No. 4,329,349 covers certain 6-$C_{1-4}$ alkyl-7-phenyl or substituted phenyl 1,6-naphthyridine-5(6H)-ones useful as muscle relaxants and as antiinflammatory agents.

V. I. Sigova and M. E. Konshin (*Khim Geterot Soed* 1984;783-5) covers a synthesis of substituted 5-oxo-5,6,7,8-tetrahydro-1,6-naphthyridines by cyclization of substituted 2-styrylnicotinic acid amides.

K.-H. Nietsch and R. Troschutz (*Arch Pharm (Weinheim)* 1985;318:175-7) covers the preparation of 7,8-dihydro-1,6-naphthyridin-5 (6H) -ones.

M. Tada and Y. Yokol (J Heterocyclic Chem 9;26:45-8) covers the synthesis of tetrahydronaphthyridinone derivatives.

J. Baldwin, et al (*J Org Chem* 1978;43:4878-80) covers a naphthyridinone synthesis via enamine cyclization.

SUMMARY OF THE INVENTION

The instant invention is novel compounds of Formula

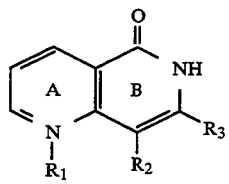

I or a pharmaceutically acceptable salt thereof wherein;
$R^1$ is absent, hydrogen, lower alkyl, or oxygen;
$R^2$ is hydrogen, alkyl, or halogen;
$R^3$ is hydrogen or alkyl; and
the—line indicates a double or single bond.

Preferred compounds of the invention are those wherein in Ring A both of the—lines indicate a double bond and in Ring B the—line indicates a double or single bond. Other preferred compounds are those wherein in Ring A the—lines indicate single bonds and in Ring B the—line is a double bond.

These compounds are useful in enhancing the lethal effects on tumor cells in warm-blood animals in that they enhance the DNA-damaging activity caused by, for example, ionizing radiation or by chemotherapeutic agents.

More preferred compounds of the instant invention on those of Formula I above wherein
$R^1$ is absent, hydrogen, methyl, or oxygen;
$R^2$ is hydrogen, bromine; and
$R^3$ is hydrogen or methyl.

Especially preferred compounds of the invention are selected from:
7-methyl-1,6-naphthyridine-5(6H) -one,
8-bromo-1,6-naphthyridine-5(6H) -one,
1,2,3,4-tetrahydro-1,6-naphthyridine-5(6H) -one,
5, 6-dihydro-1-methyl-5-oxo-1,6-naphthyridine-1-iummonoiodide,
1,2,3,4-tetrahydro-1-methyl-1,6-naphthyridine-(5(6H) -one,
1,6-naphthyridine-5 (6H) -one, 1-oxide, and
7,8-dihydro-1,6-naphthyridine-5 (6H) -one.

The present invention is also a pharmaceutical composition for potentiating tumor cells to treatment with ionizing radiation or to chemotherapy comprising a potentiating amount of a compound according to Formula I and a pharmaceutically acceptable carrier.

The present invention also concerns a method of potentiating tumor cells in a warm-blooded animal to the lethal effects of radiation comprising administering a compound according to Formula I in unit dosage form.

DETAILED DESCRIPTION OF THE INVENTION

The dihydro- and tetrahydronaphthyridones of the instant invention are a small series of water-soluble compounds which are quite easy to administer.

In the compounds of Formula I the term alkyl includes lower alkyl groups, straight or branched of from 1 to 6 carbon atoms. Especially preferred alkyls are methyl and ethyl.

The term halogen includes fluorine, chlorine, bromine, and iodines, especially preferred is bromine and chlorine.

The compounds include solvates and hydrates and pharmaceutically acceptable salts of the compounds of Formula I.

Appropriate compounds of Formula I are useful in the free base form, in the form of base salts where possible, and in the form of acid addition salts. The three forms are within the scope of the invention. In practice, use of the salt form amounts to use of the free base form. Pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively, or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine and lysine; guanidine; N-methylglucosamine; N-methylglucamine; L-glutamine; N-methylpiperazine; morpholine; ethylenediamine; N-methylpiperazine; morpholine; ethylenediamine; N-benzylphenethylamine; tri(hydroxymethyl) aminomethane; and the like. (See for example, "Pharmaceutical Salts," *J Pharm Sci* 1977; 66(1):1-19).

The acid addition salts of said basic compounds are prepared either by dissolving the free base of Compound I in aqueous or aqueous alcohol solution or other suitable solvents containing the appropriate acid or base and isolating the salt by evaporating the solution, or by reacting the free base of Compound I with an acid as well as reacting Compound I having an acid group thereon with a base such that the reactions are in an organic solvent, in which case the salt separates directly or can be obtained by concentration of the solution.

The compounds of the invention may contain an asymmetric carbon atom. Thus, where possible, the invention includes the individual stereoisomers, and mixtures thereof. The individual isomers may be prepared or isolates by methods known in the art.

Preferred compounds useful in sensitizing tumor cells as described herein are of the Formula I as defined above.

It is understood that tautomeric forms, when possible, of the compounds of Formula I are included in the invention.

The formulation and administration of the compounds of Formula I for use to sensitize tumor cells in warm-blooded animal hosts will typically be used in radiotherapy of human patients, however, the compounds of Formula I may also be used to sensitize tumor cells in other warm-blooded animal species.

Although the present invention is not meant to be limited to hypoxic tumors its utility is to include such tumors. Hypoxia is believed to be associated with all types of solid malignant neoplasms. The compounds of the invention may, therefore, be used to radiosensitize neoplastic epithelial cells, endothelial cells, connective tissue cells, bone cells, muscle cells, nerve cells, and brain cells. Examples of carcinomas and sarcomas that may be radiosensitized include carcinomas such as epithelial cells, alveolar cells, basal cell, basal squamous cell, cervical, renal, liver, Hurthle, Lucke, mucinous, and Walker, and satcomas such as Abernathy's, alveolar soft part, angiolithic, botyroid, encephaloid, endometria stroma, Ewing's fascicular, giant cell, lymphatic, Jensen's justocortical osteogenic, Kaposi's, medullary, and synovial. Specific examples of tumors that have been radiosensitized with other radiosensitizers are reported in G. E. Adams Cancer: *A Comprehensive Treatise* (F. Becker, ed), 1977;6:181-223, Plenum, New York).

The compounds of Formula I of the present invention may be administered to patients orally or parenterally (intravenously, subcutaneously, intramuscularly, intraspinally, intraperitoneally, and the like). It is likely, however, that the preferred route for human administration will be intravenous. When administered parenterally they will normally be formulated in a unit dosage injectable form (solution, suspension, emulsion) with a pharmaceutically acceptable vehicle. Such vehicles are typically nontoxic and nontherapeutic. Examples of such vehicles are water; aqueous vehicles such as saline, Ringer's solution, dextrose solution, and Hanks' solution; and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a tablet, capsule, suppository, or cachet. Such formulations typically include a solid, semi-solid, or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitan monolaurate, methyl hydroxybenzoate, propyl hydroxybenzoate, talc, and magnesium stearate.

The amount of compound administered to the subject is sufficient to radiosensitize the malignant neoplasm to be treated but below that which may elicit toxic effects. This amount will depend upon the type of tumor, the species of the subject being treated, the indication dosage intended, and the weight or body surface of the subject which can be determined by a physician of skill in the art. The radiation may be administered to humans in a variety of different fractionation regimens, i.e., the total radiation dose is given in portions over a period of several days to several weeks. These are most likely to vary from daily (i.e., five times per week) doses for up to 6 weeks, to once-weekly doses for 4 to 6 weeks. An individual dose of the compounds of Formula I of the present invention is given before each radiation treatment and is likely to be in the range of 0.01 to 20 mmol/kg and usually in the range of 0.1 to 2 mmol/kg.

Since radiosensitivity is directly related to the concentration of the administered compound in the tumor, the compounds will ideally be administered at a time such that their peak concentration in the hypoxic cells occurs at a predictable time in relation to the time the tumor is exposed to radiation. This time will depend upon the manner in which the compound is administered, the particular dosage form employed, the type of tumor, and the species of the patient. Intravenous administration will typically be done about 0.5 to 1 hour prior to radiation exposure to provide maximum radiosensitization. Oral administration may require a somewhat longer lag because the compound must first pass through the gastrointestinal barrier.

Scheme 1 below illustrates schematically the preparation of Compounds 3 through 9 of the instant invention. See Examples 1-7.

Step 1

1. Various hydrolysis conditions, both under acid and base conditions, can be used to give the acid or acid salt and are understood by those skilled in the art. Temperature range of 0°-10° C.
2. Activation of the acid salt to the acyl chloride is possible under a number of conditions known to those skilled in the art and include reaction with such agents as thionyl chloride (chloromethylene) dimethylammonium chloride, phosphorus oxychloride, phosphorus pentachloride, and the like. Additionally, activation of the acid to other acyl balidates, mixed anhydrides, acylimidazoles, acyl phosphates, and the like can be carried out under a number of conditions known to those skilled in the art. Typical solvents for this activation include chlorinated solvents, aromatic hydrocarbons, dipolar aprotic solvents such as DMF, various ethers, and lower dialkyl ketones. The temperature can vary from 0°-80° C.
3. Amidation with ammonia can be carried out by a variety of conditions known to those skilled in the art, including reaction with anhydrous NH$_3$ and 1,1,1,3,3,3-hexamethyldisilazane, and the like. Typical solvents include chlorinated solvents, various ethers, aromatic hydrocarbons, dipolar aprotic solvents, lower dialkylketones, lower alkyl acetate esters, and lower alkyl nitriles. The temperature can range from −40°-100° C.

Steps 2 and 3

1. One can utilize formamide and acetamide acetal reagents in which the alkyl moiety of the acetal can include various lower alkyl and cycloalkyl functionality such as ethyl, isopropyl, cyclohexyl, and the like, or similar agents as discussed by Abdulla RF, et al, *Tetrahedron* 1979;35:1675. The reaction can be carried out with heat or with solvents as described in the reference above. The temperature can vary from 0°-10° C.
2. Typical solvents include various ethers, dipolar aprotic solvents, and lower alkyl nitriles. Typical bases include common metal hydrides such as NaH, metal alkoxides, alkyl lithiums, and metal amides. The temperature can vary from 0°-125° C.

Step 4

Step 6

Other oxidizing agents include hydrogen peroxide, alkyl, and aromatic peracids such as m-chloroperbenzoic acid, various metal oxides such as $RuO_4$, and other methods known to those skilled in the art. Solvents include water, lower alkyl organic acids, various ethers, chlorinated hydrocarbons, dipolar aprotic solvents, lower alkyl nitriles. Temperature range of 0°-125° C.

Step 7

Typical solvents include various ethers, lower alcohols, dipolar aprotic solvents such as DMF, lower dialkyl ketones, lower alkyl nitriles. Methylating agents include various methane sulfonates such as dimethyl sulfate, higher methyl halides such as methyl iodide, and the like. Temperature range of 0°-100° C.

Step 8

Same as Step 4.

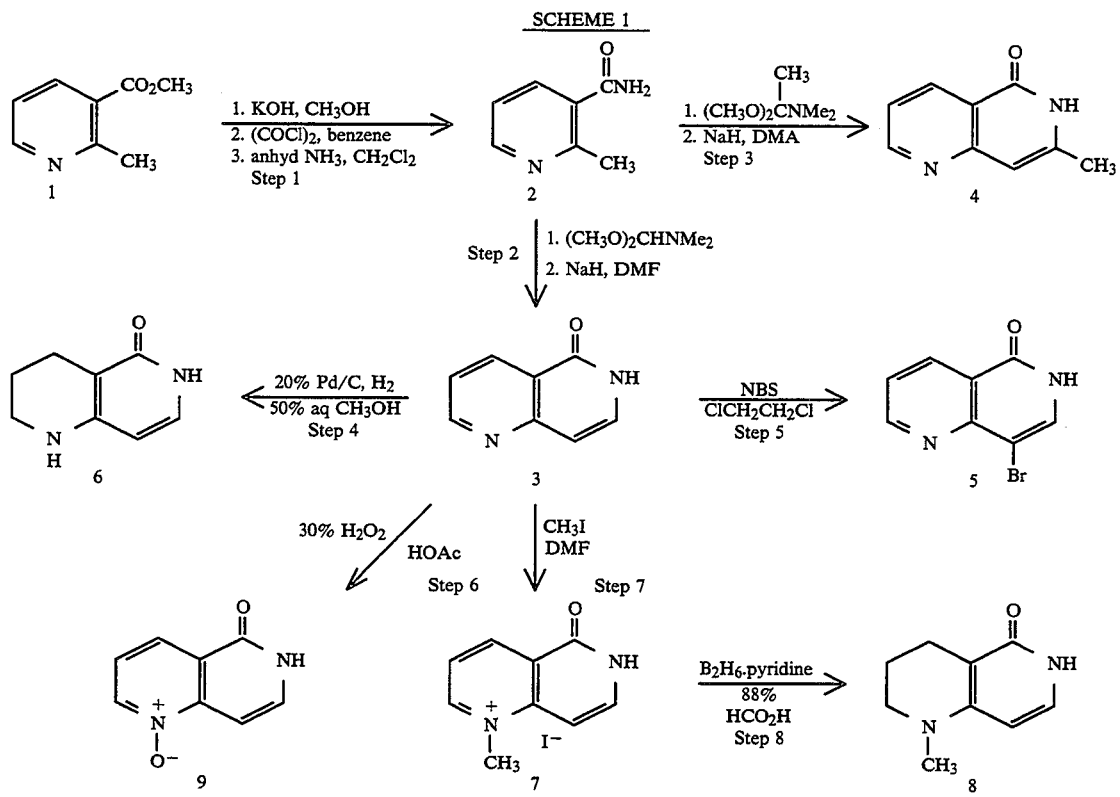

SCHEME 1

Reduction can also be carried out under catalytic hydrogenation conditions utilizing other noble metal catalysts as described in *Aldrichimica Acta* 1979:12, or with a variety of metal hydride reducing agents such as $NaBH_4$, $B_2H_6$, and the like. Suitable solvents include water, lower alcohols, ethers, lower alkyl organic acids such as acetic acid. Temperature can vary from 0°-80° C.

Step 5

Other brominating agents include bromine, complexed bromine such as pyridinium bromide perbromide, and the like. Solvents include chlorinated hydrocarbons, dipolar aprotic solvents, and various ethers. Temperature can range from 0°-100° C.

Scheme 2 below illustrates schematically the preparation of Compound 13 of the instant invention. See Example 8.

Step 1

Bases include essentially all metal bicarbonates and carbonates, especially those of Group I metals (Na, K, Rb, Cs), also common amine bases such as tertiary lower alkyl amines (triethylamine, diisopropyl ethylamine, N-Me-pyrrrolidines, etc). Also common metal bases such as NaH. Quaternary ammonium bases such as $nBu_4N^+OH^-$, etc; various fluoride bases such as $nBu_4NF$, KF, etc. Solvents include various ethers, dipolar aprotic solvents, lower dialkyl ketones, lower alkyl nitriles. Methylating agents include various methane sulfonates such as dimethyl sulfate, higher methyl halides such as methyl iodide, etc. Temperature range of 0°–100° C.

Step 2

Catalysts include various palladium (II) catalysts such as palladium chloride, bis(triphenylphosphine)palladium (II) chloride, etc and palladium (O) catalysts such as tetrakis(triphenylphosphine)palladium (O), etc. Solvents include dipolar aprotic solvents, various ethers. Temperature range of 0°–125° C.

Step 3

Ammonium salts include those of the common mineral acids and of lower alkyl organic acids. Solvents include water, lower alcohols, lower alkyl acids, various ethers, either used alone or in combination. Temperature range is 50°–180° C.

SCHEME 2

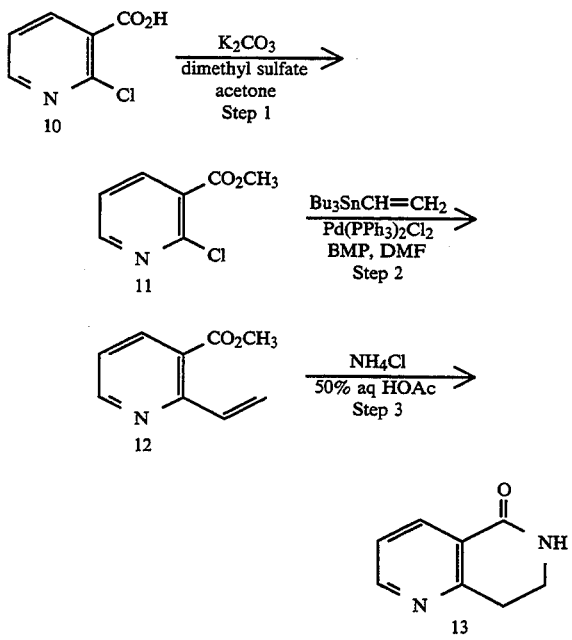

The following examples are illustrative of the instant invention, they are not intended to limit the scope of the invention.

EXAMPLE 1

1,6-Naphthyridine-5(6H)-one (3)

A mixture of 27.2 3 g ( 0.2 mol) of 2-methylnicotinamide (2) and 38.5 mL (0.263 mol) of 90% N,N-dimethylformamide dimethylacetal is heated at 50° C. for 2 hours. During the second hour, a 200 mm vacuum is applied to remove volatiles. The solution is cooled to 25° C., diluted with 200 mL of anhydrous N,N-dimethylformamide, then treated carefully with batchwise portions of 10.4 g (0.26 mol) of 60% sodium hydride (vigorous evolution of hydrogen). The mixture is brought to 80° C. where it is maintained for 2.5 hours. The suspension is cooled in ice, then treated cautiously with 50 mL of 2-propanol. The suspension is refrigerated overnight, and the precipitated solids are collected by filtration. The solids are dissolved in ca. 100 mL of hot water, and the solution is filtered. The filtrate is cooled in ice and treated dropwise with concentrated hydrochloric acid to pH 7.2. The resultant suspension is cooled for 3 hours, then the solids are collected by filtration, washed with ice-cold water, and dried over $P_2O_5$ to leave 13.89 g of pure product as an off-white solid, mp 243°–245° C.

2-Methylnicotinamide (2) is prepared as follows: to an ice-cold solution of 75.6 g (0.5 mol) of methyl 2-methylnicotinate (1) in 250 mL of methanol is added slowly 87.3 mL (0.524 mol) of 6 M aqueous potassium hydroxide. The mixture is stirred at 25° C. for 6 hours, then diluted with 100 mL of water. The solution is washed with three portions of diethyl ether, then concentrated to dryness. The resultant solid is co-evaporated several times with ethanol, suspended in ca. 250 mL of 2-propanol, and the suspension added to ca. 1.2 L of diethyl ether. The solids are collected by filtration, washed well with ether, and dried at 200 mm/90° C./14 hours over $P_2O_5$ to leave 88.6 g of potassium salt, mp >280° C.

To a mechanically stirred, ice-cold suspension of the potassium salt in 500 mL of benzene is added dropwise over 45 minutes 45.8 mL (0.525 mL) of oxalyl chloride (vigorous evolution of $CO_2$). The suspension is then stirred at 25° C. for 19 hours during which solution homogeneity results. The olive-green suspension is filtered over Celite, and the pad is washed well with methylene chloride. The filtrate is concentrated to ca. 200 mL of solution which is added as a thin stream over 5 minutes to an ice-cold solution of 500 mL of methylene chloride solution presaturated with anhydrous ammonia. An additional 150 mL of methylene chloride is utilized to transfer the acid chloride. Into the resultant cold suspension is bubbled additional ammonia over a 1-hour period. The cooling bath is removed and the mixture is stirred for 30 minutes more. The suspension is filtered and the solids are washed with methylene chloride. The filtrate is evaporated to leave additional solids which are collected as above. The solids are combined and dissolved in ca. 1.3 L of methanol. The solution is treated with 100 g of anhydrous potassium carbonate, then stirred for 15 minutes. The suspension is filtered over Celite, the filtrate evaporated to near dryness, diluted with ca. 600 mL of acetonitrile, then heated to effect solution. The hot solution is loaded onto a pad of silica gel (230–400 mesh), and the pad is washed with ethyl acetate: methanol (4:1) until all product is collected. The filtrate is concentrated to ca. 600 mL, and the resultant suspension is boiled, then filtered hot to remove some insolubles. The filtrate is cooled, the solids collected by filtration, and dried to leave 48 g of the pure product as an off-white solid, mp 156°–159° C. The mother liquor is concentrated to dryness and purified over silica gel as above to give 10.5 g of additional product as a light-yellow solid, mp 151°–154° C.

EXAMPLE 2

7-Methyl-1, 6-naphthyridine-5 (6H) -one (4)

A mixture of 272.3 mg (2 mmol) of 2-methylnicotinamide (2) and 0.34 mL (2.2 mmol) of 95% N,N-dimethylacetamide, dimethylacetal is heated at 50° C. for 1.5 hours, then a vacuum is applied for 1 hour with heating as described above. The oil is diluted with 2 mL of dry N,N-dimethylacetamide, treated with 96 mg of 60% sodium hydride, and heated at 80° C. for 2.5 hours. The solution is treated with 70 mg more of 60% sodium hydride, heated for an addition 4.5 hours, then quenched with excess acetic acid. The mixture is concentrated at 2 mm/70° C. to leave a residual solid that is triturated in hot chloroform, then filtered through a pad of silica gel (230-400 mesh). The pad is eluted with chloroform, then acetone to collect the product. The filtrate is concentrated to a solid that is dissolved in a minimum volume of hot water. The solution is stored at 5° C. for 2 weeks, and the precipitated solids are collected by filtration, washed well with propanol, and dried to give 73 mg of pure product, mp 244°-245° C.

EXAMPLE 3

8Bromo-1,6-naphthyridine-5(6H) -one (5)

A suspension of 1.462 g (10 mmol) of 1,6-naphthyridine-5(6H)-one (3), 1.96 g (11 mmol) of N-bromosuccinimide, and 30 mL of dry dichlorothane is stirred at 25° C. for 3.5 hours. The mixture is filtered, the solids are washed successively with small amounts of chloroform, water, and ether, then dried to leave 2.0 g of white solid, mp 245°-250° C. This is combined with 348 mg from an earlier run. The solids are triturated in 15 mL of hot water, collected by filtration, and dried to leave 2.28 g of pure product, mp 247°-251° C.

A suspension of 360 mg of the product in methanol is treated with an excess of 2-propanoic hydrogen chloride, heated for 3 to 5 minutes, and stored at 25° C. for 1.5 hours. The solids are collected by filtration, washed with 2-propanol, and dried to give 410 mg of yellow powder as the hydrochloride salt, mp >245° C. (decomposition).

EXAMPLE 4

1,2,3,4-Tetrahydro-1,6-naphthyridine-5(6H)-one (6)

A suspension of 400 mg of 1,6-naphthyridin-5(6H)-one (3), 40 mg of 20% palladium on carbon, and 10 mL of 50% aqueous methanol is stirred at 25° C. for 3 hours. The mixture is filtered through Celite, and the filtrate is concentrated to leave a white foam that is boiled in 2-propanol then cooled. The solids are collected by filtration, washed with 2-propanol, and dried to leave 120 mg of pure product, mp >250° C. (decomposition). Processing of the mother liquor gives 165 mg of a second crop.

Treatment of 270 mg of the free base with 2-propanoic hydrogen chloride as described above gives 210 mg of the hydrochloride salt, mp 178°-180° C.

EXAMPLE 5

5,6-Dihydro-1-methyl-5-oxo-1,6-naphthyridin-1-ium monoiodide (7)

A suspension of 5.85 g (40 mmol) of 1,6-naphthyridin-5(6H)-one (3), 10 mL of iodomethane, and 50 mL of anhydrous N,N-dimethylformamide is stirred at 25° C. for 19 hours. The suspension is treated with an additional 4 mL of iodomethane, stirred for 24 hours more, and poured slowly into 100 mL of stirring acetone. The solids are collected by filtration, washed with acetone, and dried to leave 10.54 g of pure product, mp 240°-244° C. The filtrate is concentrated in vacuo to give a solid residue that is triturated with 2-propanol and further processed to give 0.78 g of a second crop, mp 235°-240° C.

EXAMPLE 6

1,2,3,4-Tetrahydro-1-methyl-1,6-naphthyridin-5 (6H) one (8)

An ice-cold solution of 11.2 g (38.84 mmol) of 5, 6-dihydro-1-methyl-5-oxo-1,6-naphthyridin-1-ium monoiodide (7) in 18.5 mL of 88% formic acid under nitrogen is treated dropwise over a 10-minute period with 9.4 mL (93 mmol) of diborane-pyridine complex. The bath is removed and the solution is stirred for 3 days. The resultant suspension is concentrated in vacuo to leave a semisolid that is dissolved in methanol. The solution is treated with a large excess of Amberlite IRA-400 (OH), and the suspension is stirred at 25° C. for 3 hours. The resin is filtered off, and the solution is concentrated to a solid residue that is triturated in hot 2-propanol. The suspension is stored at 5° C., then the solids are collected by filtration, washed with 2-propanol, and dried to leave 5.19 g of pure product as a white solid, mp 260°-26120 C.

The filtrate is concentrated to a solid that provides 0 53 g of additional product, mp 260°-261° C. after two crystallizations.

EXAMPLE 7

1,6-Naphthyridine-5(6H)-one, 1-oxide (9)

An 80° C. solution of 239 mg (2 mmol) of 1,6-naphthyridin-5(6H)-one (3) in 2 mL of glacial acetic acid is treated sequentially with 0.3 mL, 0.2 mL, and 0.2 mL of hydrogen peroxide after 0, 1.5, and 15 hours, respectively. After a total heating time of 20 hours, the mixture is cooled and the precipitated solids are collected by filtration. The solids are dissolved in hot water, the solution diluted with methanol, and then allowed to stand at 25° C. for 4 days. The precipitated solids are collected by filtration, washed with methanol, and dried to leave 48 mg of pure product as a violet solid, mp >280° C. (decomposition).

EXAMPLE 8

7,8-Dihydro-1,6-naphthyridin-5(6H)-one (13)

A solution of 5.14 g of ca. 95% pure 2-ethenyl-3-pyridinecarboxylic acid, methyl ester (12) (ca. 30 mmol), 16.9 g (315 mmol) of ammonium chloride and 65 mL of 50% aqueous acetic acid is heated at reflux under nitrogen for 5 hours. The solution is cooled and concentrated to leave a solid residue that is triturated in hot methanol and filtered. The filtrate is treated cautiously with excess sodium hydrogen carbonate, filtered again, and concentrated to a solid that is boiled in ethyl acetate. The hot suspension is filtered and the cooled filtrate is loaded onto a 15×6 cm column of silica gel (230-400 mesh). The column is eluted with ethyl acetate followed by 600 mL of 95:5 ethyl acetate: methanol to remove nonpolar impurities, then with 1 L of 90:10 followed by 300 mL of 85:15 ethyl acetate: methanol to strip off the product. Product fractions are combined and concentrated to leave 2.1 g of a solid that is triturated in hot ethyl acetate and collected by filtration to leave 1.28 g of pure product, mp 163°-166° C.

2-Ethenyl-3-pyridinecarboxylic acid, methyl ester (12) is prepared as follows: a mixture of 19.7 g (115 mmol) of 2-chloro-3-pyridinecarboxylic acid, methyl ester (11), 38.3 g (120.8 mmol) of vinyltributyltin, 1.48 g (2.1 mmol) of bis(triphenylphosphine)palladium (II) chloride 100 mg of 2,6-ditertbutyl-4-methylphenol, and 250 mL of N,N-dimethylformamide is stirred at 55° C. for 7 hours, then treated with 1.63 g 15.1 mmol) of additional vinyltributyltin and 1 g of palladium catalyst. The mixture is heated further at 40° C. for 61 hours, then concentrated at 60° C./5 mm to leave a greenish oil that is dissolved in ethyl acetate and filtered through a pad of silica gel (230-400 mesh). The filtrate is diluted with additional ethyl acetate and the organic phase is washed with water, dried, and concentrated to an oil. The oil is distilled, with material collected in the 80°–95° C./0.14 mm ranger to leave 24.5 g of an oil that is ca. 75% product by GC. The oil is dissolved in dichloromethane:hexanes (1:1) and loaded onto an 8 x 15 cm of silica gel column (230–400 mesh). The column is eluted with the same solvent as above with 500 mL fractions collected. Product fractions are combined and carefully distilled at 65°–67° C./0.15 mm to leave 13.6 g of clear oil, >95% pure by GC, that is sufficiently pure to use directly in the next step.

2-Chloro-3-pyridinecarboxylic acid, methyl ester (11) is prepared as follows: a suspension of 22.06 g (140 mmol) of 2-chloro-3-pyridinecarboxylic acid (10), 14.6 mL (154 mmol) of dimethyl sulfate, 29 g (210 mmol) of anhydrous powdered potassium carbonate, and 140 mL of acetone is stirred at room temperature overnight. The mixture is filtered, the salts are washed with acetone, and the filtrate is concentrated to an oil that is diluted with dichloromethane. The organic phase is washed with saturated aqueous sodium dicarbonate, dried, then filtered through a pad of silica gel (230–400 mesh). The filtrate is concentrated to give an oil that is distilled at 90°–91° C./0.17 mm to leave 19.9 g of the pure product as a colorless oil.

EXAMPLE 9

Inhibition of Poly (ADP-ribose) synthetase

See Y. Shizuta, I. Seiji, K. Nakata, and O. Hayaishi, Poly(ADP-ribose) synthetase from calf thymus (Method Enzymol 1980; 66: 159–165).

Poly (ADP-ribose) synthetase is partially purified by the procedure of Shizuta, et al, up to and including the DNA-agarose column step. Active fractions are pooled and stored in small aliquots at −90° C. The specific activity was generally in the range of 25 U/rag protein, where one unit of enzyme activity is defined as the amount polymerizing 1 nmol of ADP-ribose moiety from [$^3$H]NAD per minute at 30° C.

The enzyme assay is performed by placing the following in small glass tubes kept at 4° C.: 100 μL of buffer consisting of 0.5 M Tris-HCl pH 8.0, 50 mM MgCl$_2$, and 5 mM dithiothreitol; 50 μL of 1 mM [adenine-2,8-$^3$H]nicotinamide adenine dinucleotide at a concentration of 15 μCi/mL; 100 μL of calf thymus DNA (0.3 mg/mL in water); 50 μL of calf thymus histone (Sigma, Type IIA, 0.5 mg/mL); 50 μL of inhibitor or inhibitor solvent; 150 μL of enzyme (25 μg). The components are thoroughly mixed and warmed to 30° C. in a water bath. After 15 minutes the reaction is stopped by adding 2 mL of ice cold 15% trichloroacetic acid and the tubes are placed on ice for 15 minutes. The precipitate is collected on glass fiber filters and washed five times with ice-cold 15% trichloroacetic acid. The filters are dried and radioactivity determined in a liquid scintillation counter. Table 1 below contains the results expressed as an IC$_{50}$ which is calculated by the media effect method of T. Chou and P. Talalay, Adv Enzyme Regul 1984;22:27.

TABLE I

ADPRP Inhibition by 1,6-Naphthyridine-5(6H)-ones

| Compound | IC$_{50}$ (μM) |
| --- | --- |
| (Reference Compound) | 0.11 |
| (3) | 1.0–10.0 |
| (5) | 1.0–10.0 |
| (6) | 1.0–10.0 |
| (7) | 10–100 |
| (9) | 10–100 |
| (13) | 2.5 |
| (8) | 0.51 |
| (4) | 1.2 |

EXAMPLE 10

In Vivo Assay for Radiosensitizing Activity

Mice were implanted with $1.9 \times 10^5$ Rif-1 sarcoma cells on Day 0. Treatment was on Days 6–10 and 13–17. On each treatment day the tumor-bearing limb received two doses of 2.5 Gy X-irradiation separated by 3 hours. Test compound was administered IP 30 minutes prior to the first x-ray dose on each treatment day. Effectiveness is measured by the T-C, the difference in days for the treated and control tumors, respectively, to reach 1000 mg.

Table II below shows the in vivo efficacy of certain compounds of the invention relative to treatment with x-irradiation only.

TABLE II

In Vivo Efficacy of Water Soluble ADPRP Inhibitors Against the Rif-1 Sarcoma

| Compound | Dose (mg/kg/inj) | T-C (days) |
|---|---|---|
| x-Ray Only | 2.5 Gy × 2 | 18 |
| (13) 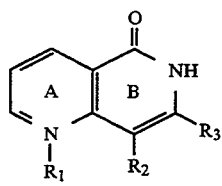 | 500 + x-Ray | 26 |
| (8) | 340 + x-Ray | 38 |

I claim:

1. A compound of Formula

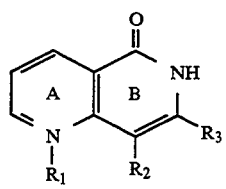

I or a pharmaceutically acceptable salt thereof wherein the — lines indicate double bonds in Ring A and in Ring B the — line indicates a single bond $R_1$ is absent,
$R_2$ is hydrogen, alkyl, or halogen;
$R_3$ is hydrogen or alkyl.

2. A compound according to claim 1 named 7,8-dihydro-1,6-naphthyridin-5(6H)-one.

3. A compound named 8-bromo-1,6-naphthyridine-5(6H)-one.

4. A compound according to claim 1 named 1,2,3,4-tetrahydro-1,6-naphthyridine-5(6H)-one.

5. A compound named 5,6-dihydro-1-methyl-5-oxo-1,6-naphthyridin-1-ium, monoiodide.

6. A compound named 1,6-naphthyridine-5(6H)-one, 1-oxide.

7. A compound named 1,2,3,4-tetrahydro-1-methyl-1,6-naphthyridin-5(6H)-one.

8. A method of sensitizing tumor cells in a warm-blooded animal to the lethal effects of radiation comprising administering to said animal in need of said sensitizing, and effective amount of a compound of formula or a pharmaceutically acceptable salt thereof wherein
$R_1$ is absent, hydrogen, or lower alkyl;
$R_2$ is hydrogen, alkyl, or halogen;
$R_3$ is hydrogen or alkyl; and
the—line indicates a double or single bond in unit dosage form.

9. A method of sensitizing tumor cells in a warm-blooded animal to the lethal effects of radiation comprising administering a compound selected from 8-bromo-1,6-naphthyridine-5(6H)-one, or 1,2,3,4-tetrahydro-1,6-naphthyridine-5(6H)-one, or 5,6-dihydro-1-methyl-5-oxo-1,6-naphthyridin-1-ium,monoiodide, or 1,6-naphthyridine-5 (6H)-one, 1-oxide, or 7,8-dihydro-1,6-naphthyridin-5(6H) -one, or 1,2,3,4-tetrahydro-1 -methyl-1,6-naphthyridin-5(6H) -one, or 7-methyl-1,6-naphthyridine-5(6H)-one in unit dosage form.

* * * * *

UNITED STATES PATENT AND TRADEMARK OFFICE
CERTIFICATE OF CORRECTION

PATENT NO. : 5,391,554
DATED : Feb. 21, 1995
INVENTOR(S) : Howard D. H. Showalter It is certified that error appears in the above-indentified patent and that said Letters Patent is hereby corrected as shown below:

Column 15, line 45, in the structure broken lines were printed as solid lines. Should be:

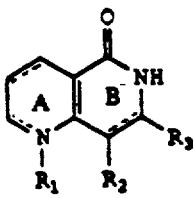

Column 16, lines 2 and 3, delete " —— " and insert instead " ---- ".

Column 16, Claim 4, line 11, delete " according to claim 1 ".

Column 16, Claim 8, line 22, delete the word "and" and insert instead the word "an".

Signed and Sealed this

Nineteenth Day of September, 1995

Attest:

BRUCE LEHMAN

Attesting Officer

Commissioner of Patents and Trademarks